US00PP22198P2

(12) United States Plant Patent
Qiu et al.

(10) Patent No.: US PP22,198 P2
(45) Date of Patent: Oct. 18, 2011

(54) ROSE PLANT NAMED 'TE JIAO'

(50) Latin Name: *Rosa hybrida*
Varietal Denomination: Te Jiao

(75) Inventors: Bao Ping Qiu, Beijing (CN); Zhang Lei, Beijing (CN); Ding Yan Li, Beijing (CN)

(73) Assignee: Beijing Union University, Beijing (CN)

( * ) Notice: Subject to any disclaimer, the term of this patent is extended or adjusted under 35 U.S.C. 154(b) by 0 days.

(21) Appl. No.: 12/804,238

(22) Filed: Jul. 16, 2010

(51) Int. Cl.
*A01H 5/00* (2006.01)

(52) U.S. Cl. ..... Plt./114

(58) Field of Classification Search ..... Plt./114
See application file for complete search history.

*Primary Examiner* — Kent L Bell
(74) *Attorney, Agent, or Firm* — Penny J. Aguirre

(57) ABSTRACT

A new cultivar of rose, 'Te Jiao', characterized by its upright, climbing habit, semi-glossy green foliage, its semi-double pink flowers, its repeat blooming habit even through hot weather, its disease resistance, and its vigorous growth habit with minimal seed production.

2 Drawing Sheets

Botanical classification: *Rosa hybrida.*
Variety denomination: 'Te Jiao'.

CROSS REFERENCE TO A RELATED APPLICATION

This application is co-pending with a U.S. Plant Patent Application filed for a plant derived in the Inventors' breeding program that is entitled Rose Plant Named 'Te Qiao' (U.S. Plant patent application Ser. No. 12/804,228).

BACKGROUND OF THE INVENTION

The present invention relates to a new and distinct cultivar of *Rosa hybrida*. The new rose will be referred to hereafter by its cultivar name, 'Te Jiao'. 'Te Jiao' is a climbing rose suitable for landscape plantings.

The new cultivar of climbing rose is a selection from a controlled breeding program conducted by the Inventors in Beijing, China with a focus on creating rose cultivars that perform well and bloom continuously in the hot summers in the northern region of China and also exhibit minimal seed production.

The new variety, 'Te Jiao', arose from a cross made in Beijing, China in 2005 between the female parent, 'Dortmund' (not patented) and the male parent, 'Beilinhong' (not patented). 'Te Jiao' was selected by the Inventors as a single unique plant from the resulting seedlings in May, 2006.

The new cultivar was first asexually propagated by the Inventors using softwood stem cuttings in Beijing, China in November, 2006. Asexual propagation using stem cuttings and tissue culture has determined that the characteristics of this cultivar are stable and are reproduced true to type in successive generations.

SUMMARY OF THE INVENTION

The following traits have been repeatedly observed and represent the characteristics of the new rose as observed in Beijing, China. These attributes in combination distinguish 'Te Jiao' as a unique cultivar of climbing rose.

1. 'Te Jiao' exhibits semi-double flowers that are pink in color.
2. 'Te Jiao' blooms continuously from April to November, even through hot summer weather.
3. 'Te Jiao' produces very few to no seeds.
4. 'Te Jiao' exhibits semi-glossy green foliage.
5. 'Te Jiao' exhibits an upright climbing habit.
6. 'Te Jiao' exhibits vigorous growth with very good disease resistance.
7. 'Te Jiao' can overwinter under natural conditions in Beijing, China.

The new cultivar of climbing rose can be readily distinguished from its parents. The female parent, 'Dortmund', has smaller single flowers that are red in color, lacks the ability to sustain flower production during hot summer months, and produces abundant clusters of fruit. The male parent, 'Beilinhong', has smaller double red flowers, exhibits a shrub habit, produces numerous seeds, and has foliage that is non-glossy. 'Te Jiao' can also be most closely compared to a cultivar from the same breeding program, 'Te Qiao', which is similar in its vigor, long blooming habit under hot summer conditions, lack of seed production and disease resistance. 'Te Qiao' differs from 'Te Jiao' in having single red-purple flowers and in having a shrub growth habit.

BRIEF DESCRIPTION OF THE DRAWING

The accompanying colored photographs illustrate the overall appearance and distinct characteristics of three year-old plants of the new rose, 'Te Jiao', as grown outdoors in a field on its own roots.

Figure 1:
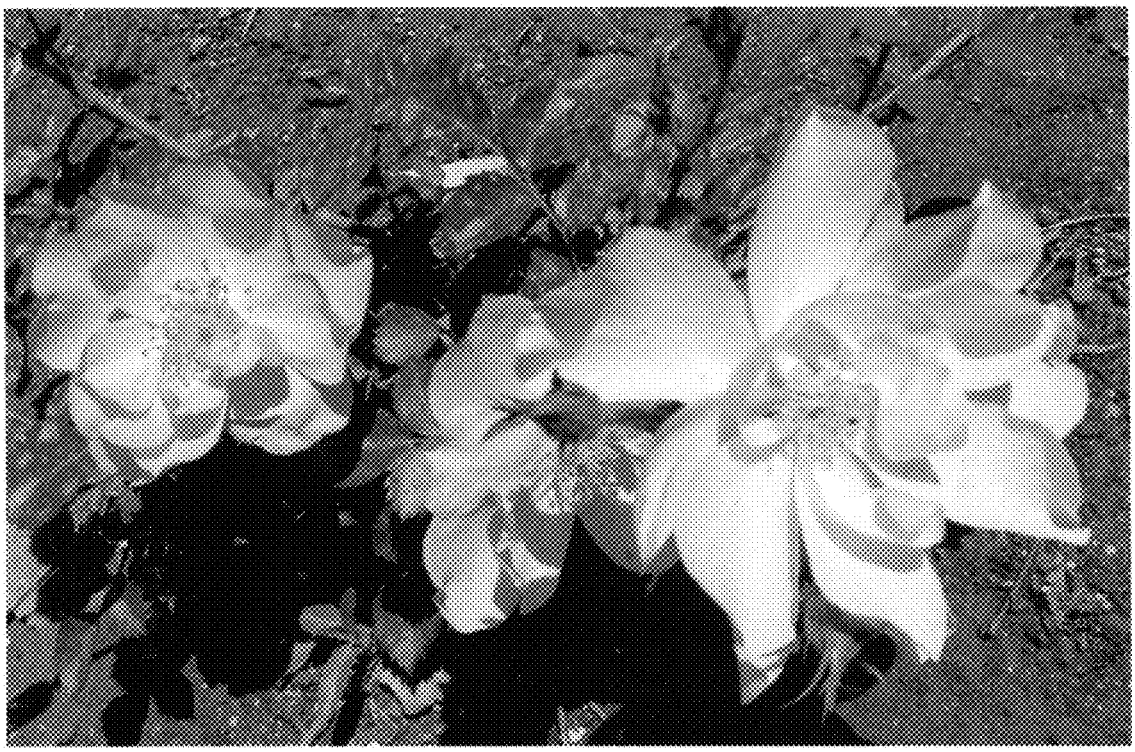
FIG. 1 provides a view of the flowers of 'Te Jiao'.
Figure 2:
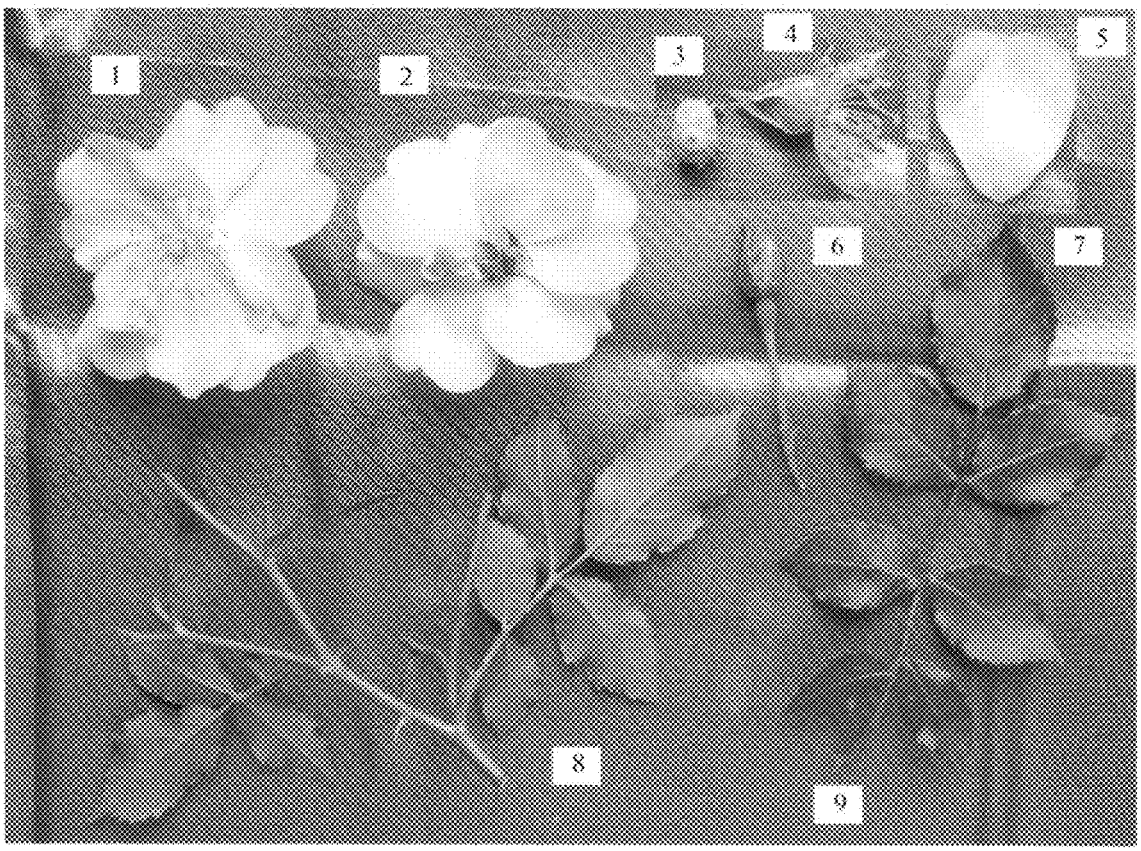
FIG. 2 provides a view of plant parts of 'Te Jiao' with labels; 1: upper surface of flower, 2: lower surface of flower, 3: receptacle, 4: reproductive organs and sepals, 5: upper surface of petal, 6: flower bud, 7 and 9: upper surface of leaf, 8: lower surface of leaf and young stem.

The colors in the photographs are as close as possible with digital photography techniques available, the color values cited in the detailed botanical description accurately describe the colors of the new rose.

DETAILED BOTANICAL DESCRIPTION

The following is a detailed description of the new cultivar as observed on 3 year-old plants as field grown in Beijing, China. Growing conditions had an average temperature of 25.8 to 24.4° C. with temperatures ranging between 12.3 and 39.6° C. and average precipitation during the months of July and August of 196.6 to 243.5 mm. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming habit.*—Repeat blooming from last week of April to mid November.

*Plant habit.*—Climbing, upright.

*Height and spread.*—Averaging 2 m in height and 1 m in spread.

*Cold hardiness.*—Can be overwintered under natural conditions in Beijing, China.

*Diseases and pests.*—Good resistance to disease and pests.

*Propagation.*—Stem cuttings and tissue culture.

*Growth.*—Vigorous.

Branch description:

*Stem color.*—Young and maturing; 145A suffused with 183D, mature wood; 146A.

*Stem surface.*—Smooth.

*Stem size.*—Average of 4 mm in width, up to 2 m in length.

*Internode.*—Average of 5 cm.

*Thorns.*—8 per 10 cm of stem, 4 mm in length, 138B in color.

Foliage description:

*Leaves.*—Division is odd-pinnate, arrangement is alternate, average of 13.0 cm in length and 6.5 cm in width.

*Leaflets.*—Ranging from 3 to 7, most frequently 7, elliptic in shape, obtuse base, acuminate apex, ciliate margins, weakly crenulate, upper surface and lower surface semi-glossy and glabrous, average of 3.5 cm in length and 2.5 cm in width, color: young leaves upper surface; 141A, young leaves lower surface: 145A, mature leaves upper surface; 139A, mature leaves lower surface; 138B.

*Venation.*—Pinnate, 183D in color on upper and lower surface.

*Rachis.*—Average of 11 cm in length and 1 to 1.5 mm in diameter, color of upper surface 138A suffused with 183D in younger tissue.

*Stipules.*—Color on upper side 139C suffused with 183D, color of lower surface is 138B.

*Petioles.*—Average of 1 mm in length and 1 mm in diameter, surface glabrous, 183D in color.

Inflorescence description:

*Inflorescence type.*—Single to corymbs of up to 4 semi-double flowers.

*Flower number.*—3 to 12 flowers per lateral stem, 1 to 7 flower buds per lateral stem, 3 to 21 flowers per plant.

*Flower fragrance.*—Moderately scented.

*Flower longevity.*—About 7 days, self-cleaning.

*Flower type.*—Semi-double, round, held upright.

*Flower size.*—Average of 6 cm in diameter and 1.5 cm in depth.

*Peduncles.*—Upright, average of 4.0 cm in length and 1.0 to 1.5 cm in diameter, glabrous to sparsely pubescent, 143C in color.

*Bracts.*—None observed.

*Flower buds.*—Ovate in shape, an average of 1.5 cm in length and 1.1 cm in width prior to opening, 61D in color.

*Sepals.*—6, lanceolate, margin weakly foliaceous appendages on 3 of the 6 sepals with stipitate glands, average of 1.8 cm in length and 7.0 mm in width, acute apex, truncate base fused with receptacle, color of lower and upper surface 143C.

*Petals.*—12 to 15 per flower, drop readily and cleanly, obcordate in shape, upper and lower surface smooth, margin crenulate, base broadly cuneate in shape, apex is rounded with indented notch, an average of 3.6 cm in length and 2.5 cm in width, color: opening flowers; upper surface 66C and lower surface 65A, fully open flowers; upper surface 66D and lower surface 65B, color retained until petal drop.

*Receptacle.*—Average of 5 mm in diameter and 6 mm in depth when flower is fully open, urn-shaped, glabrous surface, 150C in color.

*Pistils.*—About 30 per flower, 3 mm in length, stigma is an average of 1 mm in length and 0.4 mm in width and 158B in color, style is an average of 3 mm in length and 158C in color, ovary is inferior, oblong-globose in shape and 143B in color.

*Stamens.*—About 100 to 110 per flower, filaments are about 5 to 10 mm in length and 9C in color, anthers are an average of 1.0 to 1.5 mm in length and 9B in color, pollen is moderate in quantity and near 12C in color.

*Hips.*—None were observed to form to date prior to the frost date in Beijing, China.

It is claimed:

1. A new and distinct cultivar of rose plant named 'Te Jiao' as herein illustrated and described.

* * * * *

UNITED STATES PATENT AND TRADEMARK OFFICE

CERTIFICATE OF CORRECTION

PATENT NO. : PP22,198 P2
APPLICATION NO. : 12/804238
DATED : October 18, 2011
INVENTOR(S) : Ping Qiu Bao, Lei Zhang and Yan Li Ding It is certified that error appears in the above-identified patent and that said Letters Patent is hereby corrected as shown below:

On the Title page,

Incorrect format of Inventor's names:

Qui; Bao Ping (Beijing, CN), Lei; Zhang (Beijing, CN), Li; Ding Yan (Beijing, CN)

Corrected format of Inventor's names should read:

Bao; Ping Qiu (Beijing, CN), Zhang; Lei (Beijing, CN), Ding; Yan Li (Beijing, CN)

Signed and Sealed this
Twenty-second Day of November, 2011

David J. Kappos

David J. Kappos
*Director of the United States Patent and Trademark Office*